US006251656B1

(12) United States Patent
Adang

(10) Patent No.: US 6,251,656 B1
(45) Date of Patent: *Jun. 26, 2001

(54) INSECTICIDAL PROTEIN FRAGMENTS

(75) Inventor: Michael J. Adang, Madison, WI (US)

(73) Assignee: Mycogen Plant Science, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/422,833

(22) Filed: Oct. 21, 1999

Related U.S. Application Data

(60) Division of application No. 06/617,321, filed on Jun. 4, 1984, now Pat. No. 6,114,138, which is a continuation-in-part of application No. 06/535,354, filed on Sep. 24, 1983.

(51) Int. Cl.[7] .............................. C12N 1/20; C12N 15/00; C07H 21/04
(52) U.S. Cl. .................. 435/252.3; 435/252.31; 435/252.33; 435/320.1; 536/23.71
(58) Field of Search ...................... 435/252.3, 252.31, 435/252.33, 320.1; 536/23.71; 424/93.461

(56) References Cited

U.S. PATENT DOCUMENTS 4,467,036   8/1984   Schepf et al. .................. 435/317

OTHER PUBLICATIONS

Fraley et al. (1983) Advances in Gene Technology: Molecular Genetics of Plants and Animals 211–221.

Michael W. Bevan, Richard B. Flavell, Mary–Dell Chilton "A Chimaeric antibiotic resistance gene as a selectable marker for plant cell transformation" *Nature* 304:184–187.

Fraley et al. (1983) "Expression of bacterial genes in plants cells" *Proc. Natl. Acad. Sci.* 80:4803–4807.

Primary Examiner—Christopher S. F. Low
Assistant Examiner—D. Srivastava
(74) Attorney, Agent, or Firm—Saliwanchik, Lloyd & Saliwanchik

(57) ABSTRACT

The *Bacillus thuringiensis* var. kurstaki HD-73 crystal protein gene was cloned into pBR322. *E. coli* cells harboring this recombinant plasmid produced a 130 kD protoxin that was toxic to *Manduca sexta* (tobacco hornworm) larvae. Plasmids having the 3'-end of the protoxin gene deleted where also constructed. *E. coli* cells harboring these deleted plasmids produced an active, soluble 68 kD toxin, provided that the 3'-deletion had not removed sequences encoding the 68 kD toxin. The invention provides methods to produce 68 kD toxin protein by constructing partial protoxin genes encoding the toxin followed by expression of the genes in living cells. Useful plasmids and cells are also provided.

1 Claim, 9 Drawing Sheets

1 Kbp

INSECTICIDAL PROTEIN FRAGMENTS

CROSS REFERENCE TO A RELATED APPLICATION

Figure 1:
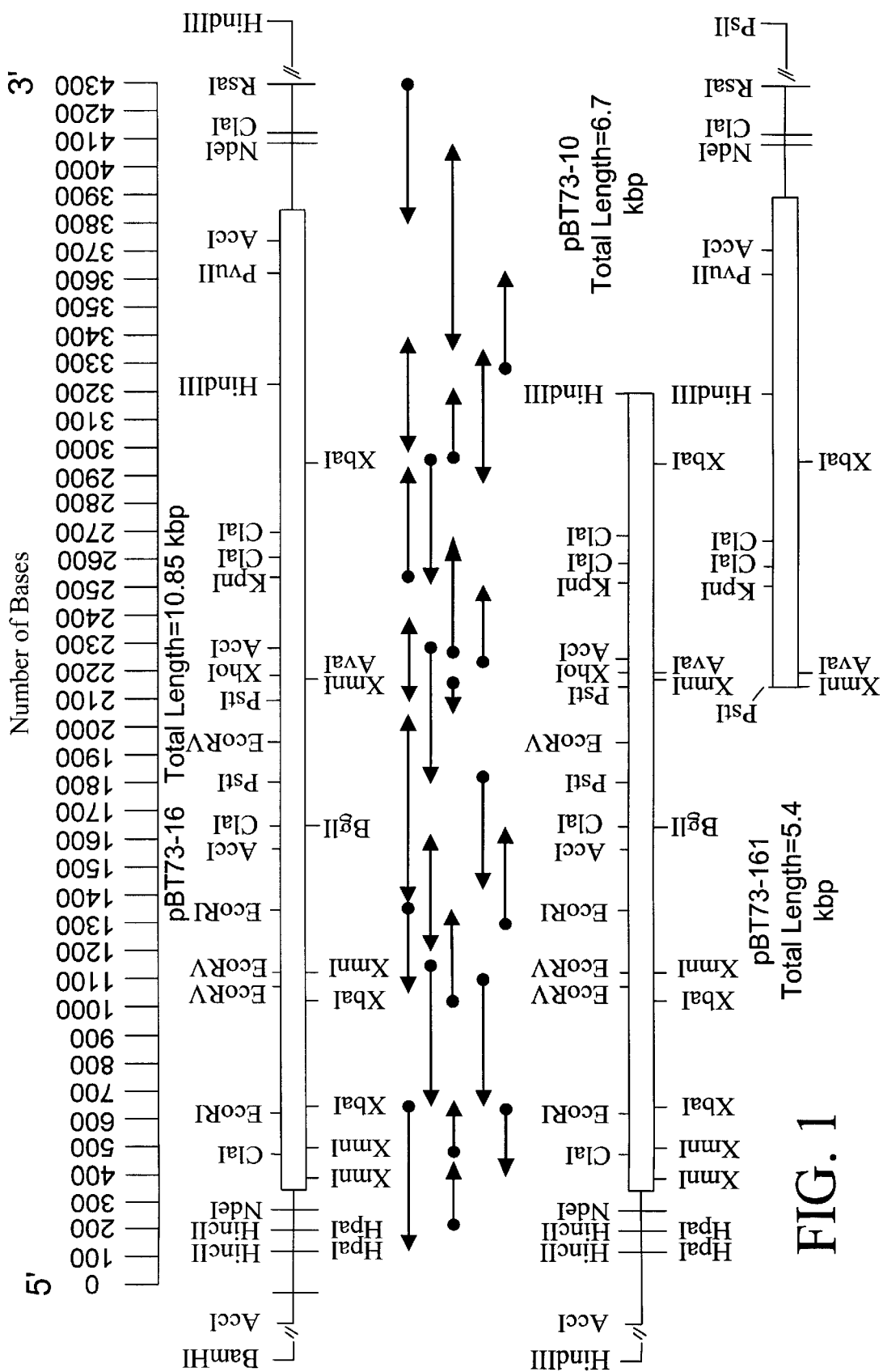
Figure 2A:
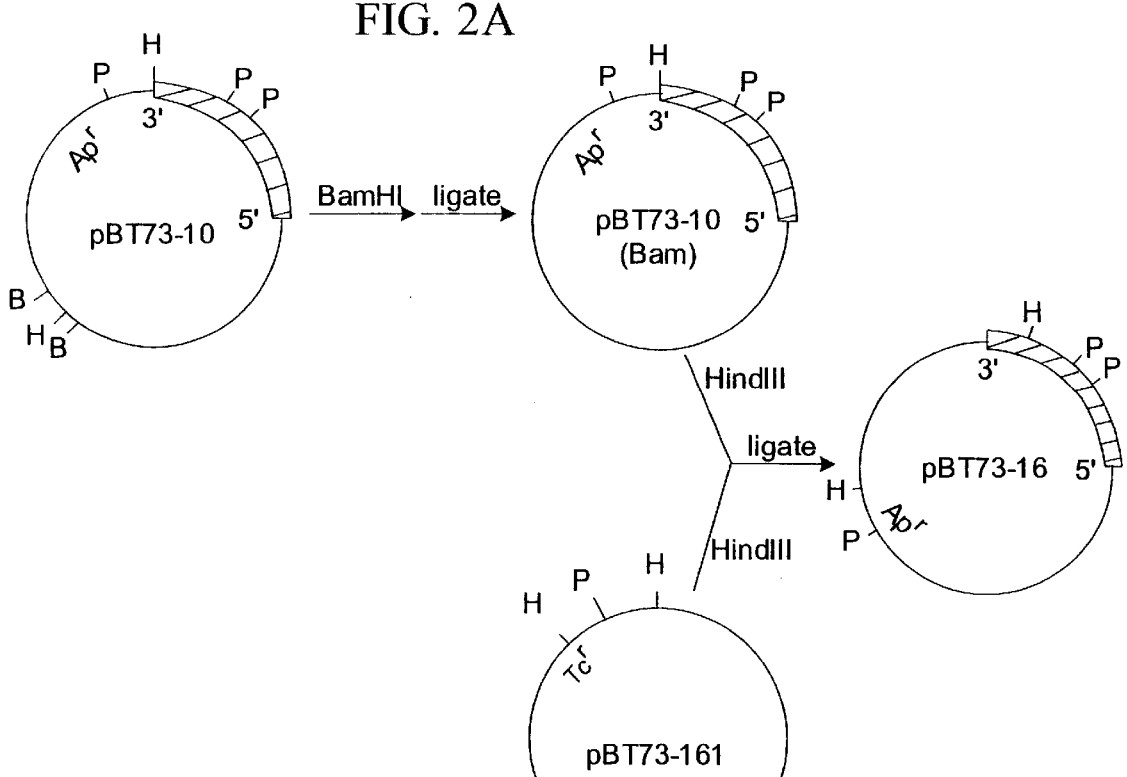
Figure 2B:
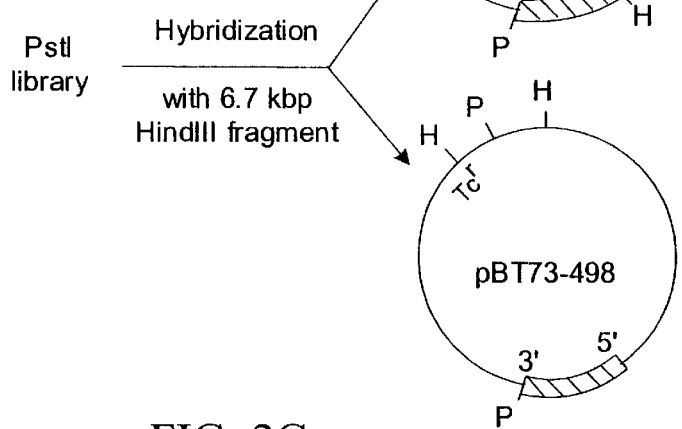
Figure 2C:
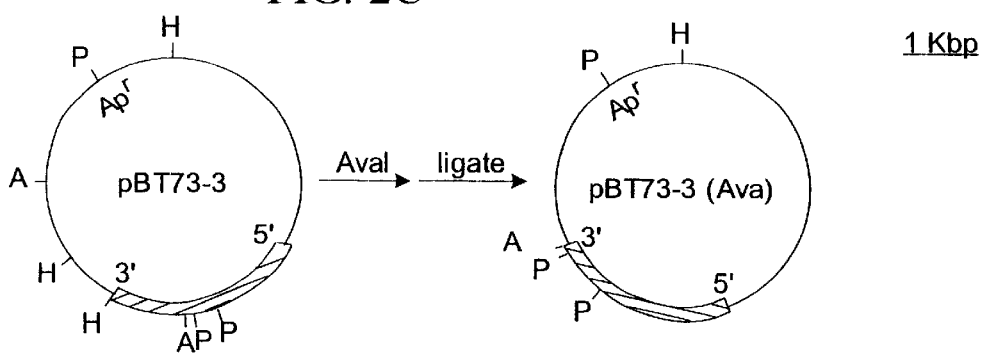

This application is a divisional of U.S. Ser. No. 06/617,321 filed Jun. 4, 1984, now U.S. Pat. No. 6,114,138 which is a Continuation-In-Part of application Ser. No. 06/535,354, filed Sep. 24, 1983.

FIELD

The present invention is in the fields of genetic engineering and bacterial bio-affecting compositions, especially those derived from the genus Bacillus.

BACKGROUND

The following are publications disclosing background information related to the present invention: G. A. Held et al. (1982) Proc. Natl. Acad. Sci. USA 77:6065–6069; A. Klier et al. (1982) EMBO J. 1:791–799; A. Klier et al. (1983) Nucl. Acids Res. 11:3973–3987; H. E. Schnepf and H. R. Whitely (1981) Proc. Natl. Acad. Sci. USA 78:2893–2897; H. E. Schnepf and X. R. Whitely, European Pat. application 63,949; H. R. Whitely et al. (1982) *Molecular Cloning and Gene Regulation in Bacilli,* eds: A. T. Ganesan et al., pp. 131–144; H. C. Wong et al. (1983) J. Biol. Chem. 258:1960–1967. R. M. Faust et al. (1974) J. Invertebr. Pathol. 24:365–373, T. Yamamoto and R. E. McLaughlin (1981) Biochem. Biophys. Res. Commun. 103:414–421, and H. E. Huber and P. Luthy (1981) in *Pathogenesis of Invertebrate Microbiol. Diseases,* ed.: E. W. Davidson, pp. 209–234, report production of activated toxin from crystal protein protoxin. None of the above publications report that partial protoxin genes when transcribed and translated produced insecticidal proteins as disclosed herein. These publications are discussed in the Background section on Molecular Biology. S. Chang (1983) Trends Biotechnol. 1:100–101, reported that the DNA sequence of the HD-1 gene had been publicly presented, (ref. 5 therein), and that the HD-1 toxin moiety resides in the amino-terminal 68kD peptide. M. J. Adang and J. D. Kemp, U.S. patent application Ser. No. 535,354, which is hereby incorporated by reference, described a plasmid, p123/58–10 therein, pBt73-10 herein, containing a partial protexin gene that, when transformed into *E. coli,* directed synthesis of an Insecticidal protein. M. J. Adang and J. D. Kemp, supra, and R. F. Barker and J. D. Kemp, U.S. patent application Ser. No. 553,786, which is hereby incorporated by reference, both teach expression of the same pBt73-10 partial protoxin structural gene in plants cells. Detailed comparisons of results disclosed as part of the present application with published reports are also detailed herein in the Examples, especially Example 5.

Chemistry

*Bacillus thuringiensis,* a species of bacteria closely related to *B. cereus,* forms a proteinacious crystalline inclusion during sporulation. This crystal is parasporal, forming within the cell at the end opposite from the developing spore. The crystal protein, often referred to as the δ-endotoxin, has two forms: a nontoxic protoxin of approximate molecular weight (MW) of 130 kilodaltons (kD), and a toxin having an approx. MW of 68 kD. The crystal contains the protoxin protein which is activated in the gut of larvae of a number of insect species. M. J. Klowden et al. (1983) Appl. Envir. Microbiol. 46:312–315, have shown solubilized protoxin from *B. thuringiensis* var. israelensis is toxic to *Aedes aegypti* adults. A 65kD "mosquito toxin" seems to be isolatable without an activation step from crystals of HD-1 (T. Yamamoto and R. E. McLaughlin (1981) Biochem. Biophys. Res. Commun. 103:414–421). During activation, the protoxin is cleaved into two polypeptides, one or both of which are toxic. In vivo, the crystal is activated by being solubilized and converted to toxic form by the alkalinity and proteases of the insect gut.

In vitro the protoxin may be solubilized by extremely high pH (e.g. pH 12), by reducing agents under moderately basic conditions (e.g. pH 10), or by strong denaturants (guanidium, urea) under neutral conditions (pH 7). Once solubilized, the crystal protein may be activated in vitro by the action of the protease such as trypsin (R. M. Faust et al. (1974) J. Invertebr. Pathol. 24:365–373). Activation of the protoxin has been reviewed by H. E. Huber and P. Luthy (1981) in *Pathogenesis of Invertebrate Microbiol. Diseases,* ed.: E. W. Davidson, pp. 209–234. The crystal protein is reported to be antigenically related to proteins within both the spore coat and the vegetative cell wall. Carbohydrate is not involved in the toxic properties of the protein.

Toxicology

*B. thuringiensis* and its crystalline end in are useful because the crystal protein is an insecticidal protein known to be poisonous to the larvae of over a hundred of species of insects, most commonly those from the orders Lepidoptera and Diptera. Insects susceptible to the action of the *B. thuringiensis* crystal protein include, but need not be limited to, those listed in Table 1. Many of these insect species are economically important pests. Plants which can be protected by application of the crystal protein include, but need not be limited to, those listed in Table 2. Different varieties of *B. thuringiensis,* which include, but need not be limited to, those listed in Table 3, have different host ranges (R. M. Faust et al. (1982) in *Genetic Engineering in the Plant Sciences,* ed. N. J. Panapolous, pp. 225–254); this probably reflects the toxicity of a given crystal protein in a particular host. The crystal protein is highly specific to insects; in over two decades of commercial application of sporulated *B. thuringiensis* cells to crops and ornamentals there has been no known case of effects to plants or noninsect animals. The efficacy and safety of the endotoxin have been reviewed by R. M. Faust et al., supra. Other useful reviews include those by P. G. Fast (1981) in *Microbial Control of Pests and Plant Diseases,* 1970–1980, ed.: H. D. Burges, pp. 223–248, and H. E. Huber and P. Luthy (1981) in *Pathogenesis of Invertebrate Microbial Diseases,* ed.: E. W. Davidson, pp. 209–234.

Molecular Biology

The crystal protein gene usually can be found on one of several large plasmids that have been found in Bacillus thuringiensis, though in some strains it may be located on the chromosome (J. W. Kronstad et al. (1983) J. Bacteriol. 154:419–428; J. M. Gonzalez Jr. et al. (1981) Plasmid 5:31–365). Crystal protein genes have been cloned into plasmids that can grow in *E. coli* by several laboratories.

Whiteley's group (H. R. Whiteley et al. (1982) in *Molecular Cloning and Gene Regulation in Bacilli,* eds.: A. T. Ganesan et al., pp. 131–144, H. E. Schnepf and H. R. Whiteley (1981) Proc. Natl. Acad. Sci. USA 78:2893–2897, and European Pat. application 63,949) reported the cloning of the protoxin gene from *B. thuringiensis* var. kurstaki strains HD-1-Dipel and HD-73, using the enzymes Sau3AI (under partial digest conditions) and BglII, respectively, to insert large gene-bearing fragments having approximate sizes of 12 kbp and 16 kbp into the BamHI site of the *E. coli* plasmid vector pBR322. The HD-1 crystal protein gene was observed to be contained within a 6.6 kilobase pair (kbp) HindIII fragment. Crystal protein which was toxic to larvae, immunologically identifiable, and the same size as authentic protoxin, was observed to be produced by transformed *E. coli* cells containing pBR322 derivatives having such large DNA segments containing the HD-1-Dipel gene or subclones of that gene. This indicated that the Bacillus gene was transcribed, probably from its own promoter, and translated in *E. coli.* Additionally, this finding suggested that the toxic activity of the protein product is independent of the location of its synthesis. That the gene was expressed when the fragment containing it was inserted into the vector in either orientation suggests that transcription was controlled by its own promoter. Whiteley et al., supra, reported a construction deleting the 3'-end of the HD-1 toxin coding sequences along with the nontoxin coding sequence of the protoxin. The transcriptional and translational start sites, as well as the deduced sequence for the amino-terminal 333 amino acids of the HD-1-Dipel protoxin, have been determined by nucleic acid sequencing (H. C. Wong et al. (1983) J. Biol. Chem. 258:1960–1967). The insecticidal gene was found to have the expected bacterial ribosome binding and translational start (ATG) sites along with commonly found sequences at −10 and −35 (relative to the 5'-end of the mRNA) that are involved in initiation of transcription in bacteria such as *B. subtilis.* Wong et al., supra localized the HD-1 crystal protein gene by transposon mutagenesis, noted that transposon insertion in the 3'-end of the gene could result in production in *E. coli* of 68kD peptides, but did not report any insecticidal activity to be associated with extracts of strains that produce 68kD peptides while lacking 130 kD protoxin.

A. Klier et al. (1982) EMBO J. 1:791–799, have reported the cloning of the crystal protein-gene from *B. thuringiensis* strain berliner 1715 in pBR322. Using the enzyme BamHI, a large 14 kbp fragment carrying the crystal protein gene was moved into the vector pHV33, which can replicate in both *E. coli* and Bacillus. In both *E. coli* and sporulating *B. subtilis,* the pHV33-based clone directed the synthesis of full-size (130 kD) protoxin which formed cytoplasmic inclusion bodies and reacted with antibodies prepared against authentic protein. Extracts of *E. coli* cells harboring the pBR322 or pHV33-based plasmids were toxic to larvae. In further work, A. Klier et al. (1983) Nucleic Acids Res. 11:3973–3987, have transcribed the berliner crystal protein gene in vitro and have reported on the sequence of the promoter region, together with the first 11 codons of the crystal protein. The bacterial ribosome binding and translational start sites were identified. Though the expected "−10" sequence was identified, no homology to other promoters has yet been seen near −35.

G. A. Held et al. (1982) Proc. Natl. Acad. Sci. USA 77:6065–6069 reported the cloning of a crystal protein gene from the variety kurstaki in a phage X-based cloning vector Charon4A. *E. coli* cells infected with one of the Charon clones produced antigen that was the same size as the protoxin (130 kD) and was toxic to larvae. A 4.6 kbp EcoRI fragment of this Charon clone was moved into pHV33- and an *E. coli* plasmid vector, pBR328. Again, 130 kD antigenically identifiable crystal protein was produced by both *E. coli* and *B. subtilis* strains harboring the appropriate plasmids. A *B. thuringiensis* chromosomal sequence which cross-hybridized with the cloned crystal protein gene was identified in *B. thuringiensis* strains which do not produce crystal protein during sporulation.

SUMMARY

In pursuance of goals detailed below, the present invention provides DNA plasmids carrying partial protoxin genes, a partial protoxin being a polypeptide comprising part of the amino acid sequence of naturally-occurring toxin and often other amino acid sequences but lacking some of the naturally-occurring protoxin amino acid sequences. These genes are expressible in *E. coli* and Bacillus. Unexpectedly, the partial protoxins produced by these genes as disclosed herein have proven to be toxic to insect larvae. Methods useful toward construction of partial protoxin genes and expression of partial protoxin proteins are also provided. The partial protoxin proteins have properties that are advantageous in use, over naturally-occurring crystal protein.

The *Bacillus thuringiensis* crystal protein is useful as an insecticide because it is highly specific in its toxicity, being totally nontoxic against most nontarget organisms. As the crystal protein is crystalline and therefore is of a particulate nature, and as it is a protoxin, the crystal protein is not water-soluble or active unless previously subjected to chemical and enzymatic treatments that solubilize and activiate it. As protoxin crystals must be ingested for toxicity, the crystal must be located where they will be eaten by larvae, while a diffusable activated toxin can have toxic effects over a more diffuse region. Also, one need not take precautions against the settling out of solution of soluble crystal protein derivatives. It is an object of the present invention to provide directly a water-soluble crystal protein derivative or toxin thereby bypassing inconvenient prior art methods of solubilization and activation. Biological synthesis of partial protoxin gene products is also advantageous over synthesis of complete protoxin, as synthesis of the partial protoxin, having a lower molecular weight than a complete protoxin, constitutes a lesser drain on the metabolic resources of the synthesizing cell. Also, transformation and expression of partial protoxin genes avoids the formation of crystalline protoxin-containing inclusion bodies within cells, e.g. plant cells, that may disrupt cellular function or prove otherwise deleterious to an organism producing a crystalline insecticidal protein.

BRIEF DESCRIPTION OF THE FIGURES

FIG. 1 presents both restriction endonuclease maps and the sequencing strategy employed to sequence the *B. thuringiensis* var. kurstaki HD-73 crystal protein gene. The dots indicate the position of the 5'-end labeling and the arrows indicate the direction and extent of sequencing pBt73-16 contains a fusion of crystal protein coding sequences from pBt73-10 and pBt73-161;

FIG. 2 diagrams the construction of plasmids containing complete or partial *B. thuringiensis* var. kurstaki HD-73 protoxin genes. A: Ligation of pBt73-10, having the 5'-end of the protoxin gene, to a pBt73-161 HindIII fragment containing the 3'-end of the gene to construct pBt73-1.6; B: AvaI fragment removal from pBt73-3 to generate a partial protoxin gene; C: pBt73-498 isolated from a *B. thuringiensis* var. kurstaki HD-73 PstI library containing a partial protoxin gene.

Figure 3D:
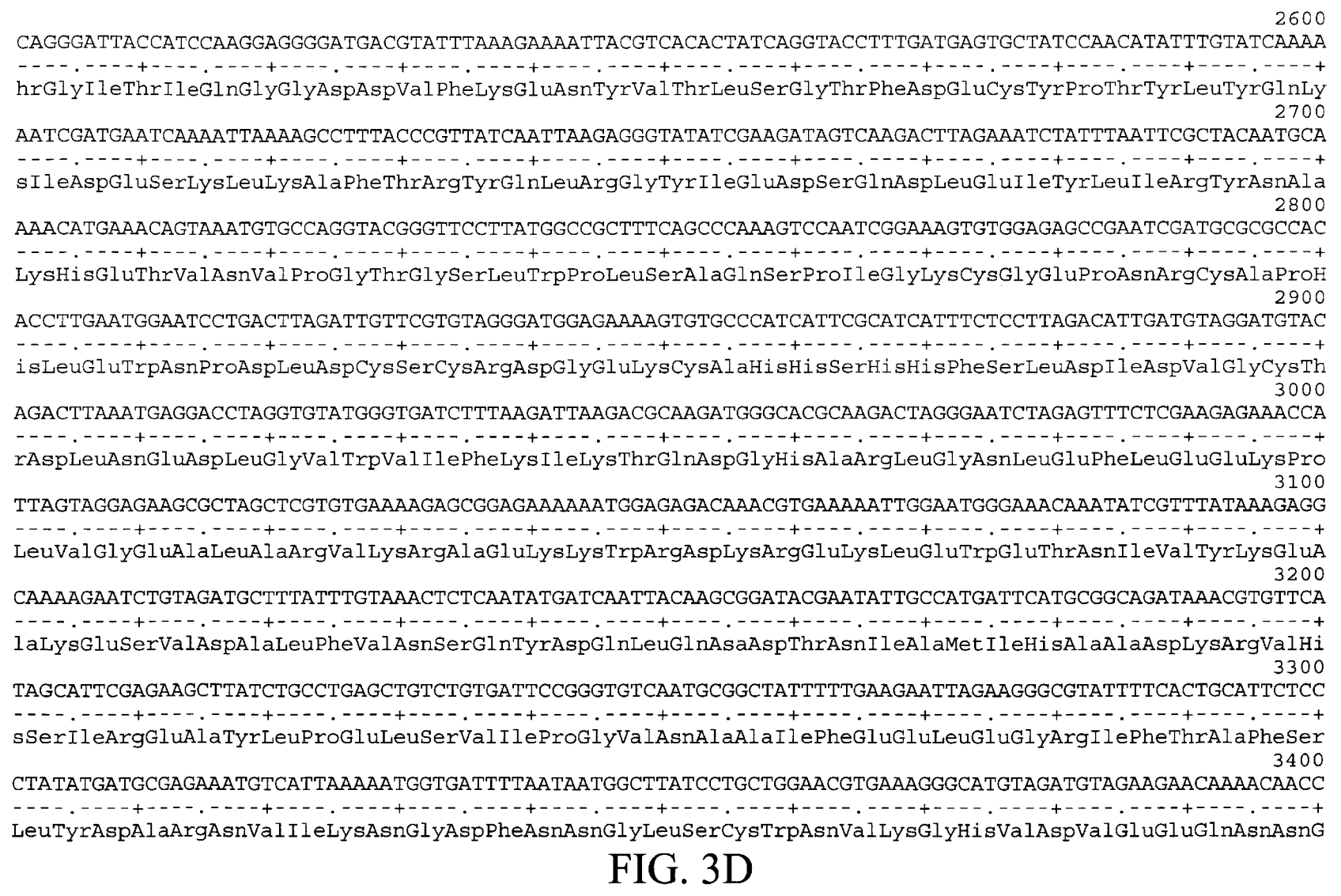

FIG. 3 discloses the complete nucleotide sequence of the *B. thuringiensis* var. kurstaki HD-73 protoxin gene. The derived amino acid sequence is given below.

Figure 4B:
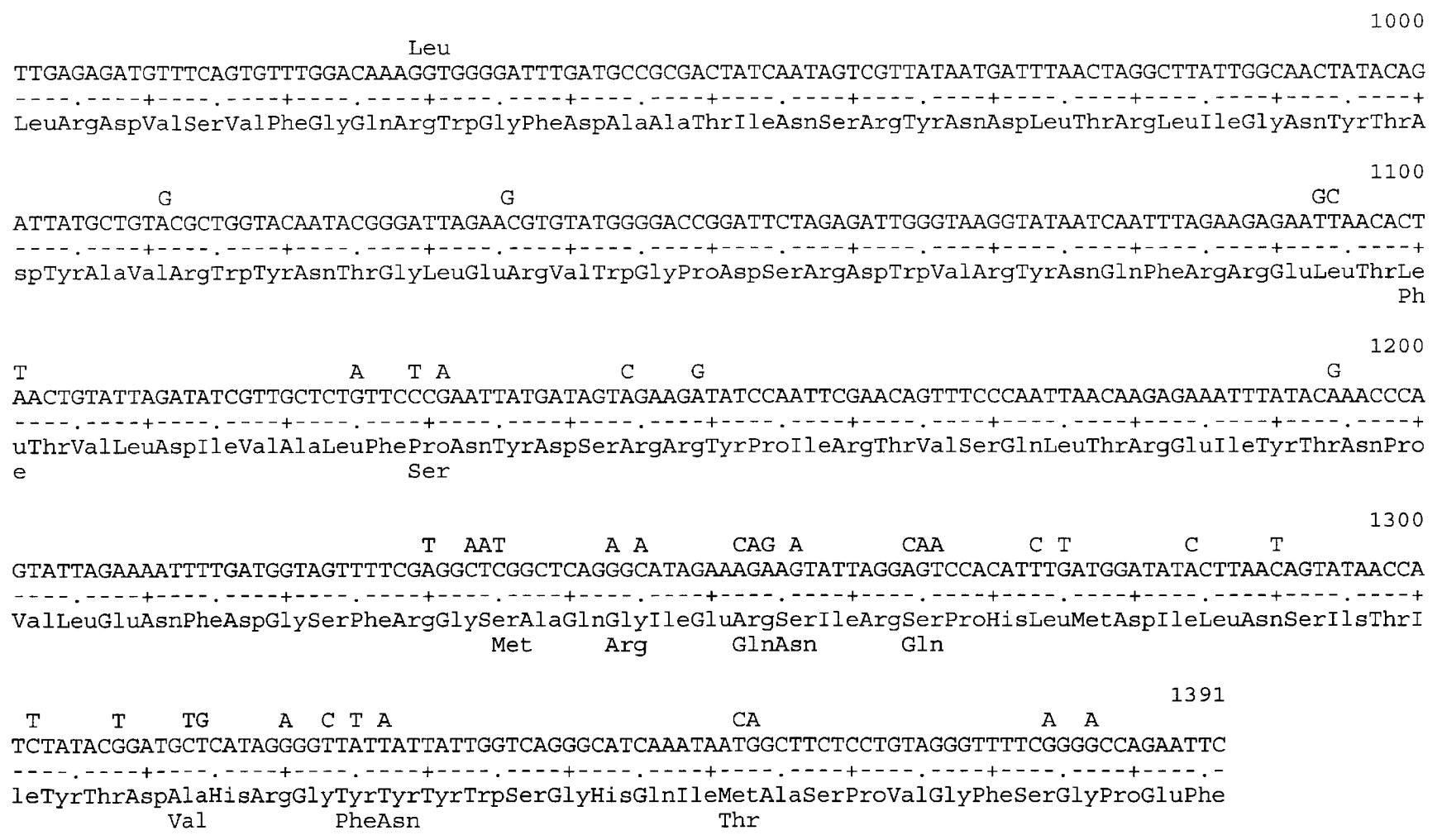

FIG. 4 compares the complete HD-73 protoxin gene sequence disclosed herein (FIG. 3) with a published partial sequence of the HD-1-Dipel crystal protein gene (H. C. Wong et al. (1983) J. Biol. Chem. 258:1960–1967). Differences between the sequences are indicated by the base and amino acid changes, the type sequence being that disclosed herein. The numbering corresponds to that of FIG. 3.

DETAILED DESCRIPTION OF THE INVENTION

The following definitions are provided in order to remove ambiguities to the intent or scope of their usage in the specification and claims.

Complete protoxin, or protoxin, refers herein to a protein encoded by a *B. thuringiensis* crystal protein gene. In the variety kurstaki, the complete protoxin has an approximate molecular weight of 130,000 Daltons.

Complete toxin, or toxin, refers herein to an insecticidal protein derived from a crystal protein, in particular, that part of the protoxin that is refractory towards processes, such as proteolytic digestion, that activiate protoxin in nature. In the variety kurstaki, the complete protoxin has an approximate molecular weight of 68,000 Daltons and is lacking the carboxy-terminal half of the protoxin.

Partial protoxin refers herein to a protein having part of the amino acid sequence of protoxin and lacking part of the amino acid sequence of the carboxy-terminus of the protoxin but not the carboxy-terminus of the toxin. Modifications of protoxin amino acid sequence, including a deletion at the amino-terminus of the toxin, may or may not be present. The partial protoxin may have at its carboxy-terminus an amino acid sequence not present in the complete protoxin. In other words, a structural gene open reading frame encoding partial protoxin may be lacking sequences encoding the carboxy terminus of the protoxin but not sequences encoding the carboxy-terminus of the toxin, and may include sequences coding for additional amino acids not present in the complete protoxin.

Complete protoxin gene, partial protoxin gene, and toxin gene refer herein to structural genes encoding the indicated proteins, each structural gene having at its 5'-end a 540 . . . ATG . . .3' translational start signal and at its 3'-end a translational stop signal (TAG, TGA, or TAA). As is well understood in the art, the start and stop signals must be in the same reading frame, i.e. in the same phase, when the mRNA encoding a protein is translated, as translational stop codons that are not in frame are ignored by the translational machinery and are functionally nonexistant. Modifications of the genetic structure, e.g. insertion of an intron that in a eukaryotic cell would be spliced out of the RNA transcript, are not excluded as long as the designated protein is encoded by the transcript Underlying the present invention is a surprising discovery: that the carboxy-terminal half of the crystal protein protoxin, encoded by the 3'-half of the protoxin gene, is not necessary for toxicity, and that a variety of protoxin gene products missing the natural carboxy-terminus (i.e. partial protoxin gene products) are processed in vivo in *E. coli* to a polypeptide essentially indistinguishable from in vivo or in vitro proteolytically-derived toxin. This last aspect constrains the sequence of the partial protoxin gene; partial protoxin gene sequences 3' from the codon encoding the carboxy-terminus of the complete toxin are removed.

Production of an insecticidal protein by means of expression of a partial protoxin gene combines specific teachings of the present disclosure with a variety of techniques and expedients known in the art. In most instances, alternative expedients exist for each stage of the overall process. The choice of expedients depends on variables such as the choice of *B. thuringiensis* strain and protoxin gene starting materials, means for and particulars of premature translational termination, vector carrying the artificial partial protoxin gene, promoters to drive partial protoxin gene expression, and organisms into which the partial protoxin gene/promoter combination is transformed and expressed. Many variants are possible for intermediates and intermediate steps, such as organism vector and DNA manipulation strategy.

In the practice of this invention one will ordinarily first obtain a recombinant DNA molecule carrying a complete protoxin gene or a fragment of a protoxin gene. The means for constructing such recombinant DNA molecules are well known in the art. If the desired protoxin is carried by a Bacillus plasmid, one may prepare DNA enriched for the gene by first isolating that plasmid, as has been exemplified herein. Alternatively, one may make a collection of recombinant DNA-containing strains from total *B. thuringiensis* DNA that is statistically likely to have at least one representative of a protoxin gene (i.e. a genomic clone library). The Bacillus DNA may be digested to completion with a restriction endonuclease that cleaves DNA rarely (a six-base-cutter like HindIII or PstI averages one site in about 4 kbp) or may be digested incompletely (i.e. partial digestion) with an enzyme that cleaves often (a four-base-cutter like Sau3AI averages one site in about 0.25 kbp), adjusting digestion conditions so the cloned DNA fragments are large enough to be likely to contain a complete protoxin gene. The Bacillus DNA is then ligated into a vector. Commonly the vector is one that can be maintained in *E. coli,* though vectors maintainable in Bacillus species are also useful. The Bacillus DNA/vector combinations are then transformed into appropriate host cells. After a collection of candidates are created, a strain containing a protoxin gene/vector combination may be identified using any of a number expedients known to the art. One can grow candidates on nitro-cellulose membrane filters, lyse the cells, fix the released DNA to the filters, and identify colonies containing protoxin DNA by hybridization. The hybridization probe can be derived from sources including a different cloned cross-hybridizing protoxin gene, sporulation-stage specific *B. thuringiensis* RNA, or a synthetic nucleic acid having a protoxin sequence deduced from the protoxin amino acid sequence. If the protoxin gene is expressed in its host, screening using bioassays for insecticidal activity or using immunological methods is possible. Immunological methods include various immunoassays (e.g. radioimmunoassays and enzyme-linked immunoassays) and a method analogous to the probing of nitrocellulose-bound DNA. Colonies grown on nitrocellulose filters are lysed, protein is bound to the filters, and colonies containing protoxin protein are identified using enzyme- or radioisotope-labeled antibodies.

The construction of recombinant DNA molecules containing complete protoxin genes, partial protoxin genes, and incomplete toxin genes can become inextricably tied to each other. Indeed, in the experimental work described herein, the original intention was to isolate a complete protoxin gene before creating and biologically testing variants deleted in their 3'-sequences. Though published studies suggested an HD-73 protoxin gene to be located completely on an approximately 6.7 kbp HindIII (H. R. Whitely et al. (1982) in *Molecular Cloning and Gene Regulation in Bacilli,* eds. A. T. Ganesan et al., pp. 131–144), the HD-73 gene isolated herein was discovered to be interrupted by a HindIII site resulting in loss of the 3'-end of the protoxin gene during HindIII digestion, e.g. as in pBt73-10 and pBt73-3. An extreme case of 3I-deletion is when sequences encoding the carboxy-terminus of the toxin are missing from the initially cloned gene fragment, resulting in lack of insecticidal activity in the expressed polypeptide, e.g. as in pBt73-498. Similar events can lead to isolation of gene fragments lacking 5'-sequences, e.g. as in pBt73-161. Conversely, should one intend to construct a partial protoxin gene, initially a complete protoxin gene may fortuitously be isolated. The isolation of missing gene fragments and their use in reconstruction of larger partial genes and complete genes is well understood in the art of recombinant DNA manipulations and is exemplified herein. Generally, one uses the gene fragment one already has to make a probe that is then used to look for flanking sequences that overlap with the probe. Libraries made using partial restriction enzyme digestion conditions can be screened directly for Bacillus DNA fragments overlapping with the probe. Libraries made using complete restriction enzyme digestion must have been made using a different enzyme than was used to make the probe-supplying plasmids. As is understood in the art, it is advantageous to map flanking restriction sites by means of Southern blots before constructing a second library. It is also advantageous to sequence or otherwise characterize the overlaps so as to be sure the two fragments are derived from the same gene, and to sequence the suture between the two fragments so as to be sure that the fusion has been accomplished as planned and that the open reading frame has been preserved, e.g. that no frameshift mutations have been introduced.

A partial protoxin gene is a protoxin generating naturally-occurring coding sequence removed from its 3'-end. By definition, a coding sequence is terminated at its 3'-end by a translational stop signal. Removal of a 3'-end sequence entails translational termination at a new site and, as the stop signal is approached, may entail departure from the naturally-encoded protoxin amino acid sequence. Coding sequences can be removed in several ways. The native stop signal need not be physically deleted; it need only be made inaccessable to ribosomes translating a protoxin-encoding mRNA transcript. One means for making the native stop inaccessible is by introduction of a frameshift mutation, usually an insertion or deletion of one or two base pairs, 5'-to the native translational stop site, thereby shifting the native stop out of the reading frame of the toxin and shifting another TAA, TAG, or TGA sequence into the toxin's reading frame. Another means for making the native stop site inaccessible is by substitution of one to three base pairs, or insertion of a stop signal, 5'-to the native stop, thereby directly creating a stop codon at that site. As is well understood in the art, substitutions and frameshift mutations can be introduced by a number of methods, including oligonucleotide-directed, site-specific mutagenesis. Frameshift mutations may also be created by cleaving DNA with a sticky-end-generating restriction enzyme followed by converting the sticky-ends to blunt-ends and religation. A number of embodiments involve deleting nontoxin protoxin sequences from the 3'-half of the protoxin gene. If the deletion is flanked on either side by protoxin gene sequences, the deletion may introduce a frameshift leading to utilization of a new stop codon. If the deletion preserves the reading frames, it will lead to utilization of the naturally used stop codon while deleting part of the nontoxin protoxin gene sequence. Should the deletion remove the 3'-end of the protoxin structural gene, the open reading frame defined by the toxin will run into nonprotoxin DNA sequences and will eventually terminate in a stop codon in that reading frames (i.e. a stop codon in frame). Nonprotoxin Bacillus DNA, vector DNA, synthetic oligonucleotides, and DNA naturally functional in a eukaryotic cell additionally having a polyadenylation site (i.e. a site determining in a eukaryotic cell the 3'-end of a transcript) 3'-to the stop codon, are all examples of nonprotoxin DNAs that may encode a partial protoxin stop codon.

As one of the goals of this invention is to express the partial protoxin gene in a living cell, the artificially constructed partial protoxin gene must be under control of a promoter capable of directing transcription in the desired cell type, a consideration well understood in the art. Generally, one uses the recombinant DNA techniques to place the structural gene and a promoter, the latter being known to drive transcription in the cell in which expression is desired, in such position and orientation with respect to one another that the structural gene is expressed after introduction into recipient cell. A special case is when during the isolation of the protoxin structural gene, a protoxin gene promoter is-isolated along with the protoxin structural gene, the protoxin promoter being the promoter which in *B. thuringiensis* drives the expression of the protoxin gene. As part of the present invention, the promoter/protoxin gene combination, which may also be referred to as a Bacillus-expressible complete protoxin- gene, was found to drive expression in *E. coli* of complete and partial protoxin genes. In Bacillus this HD-7.3 promoter drives protoxin gene transcription only during sporulation.

The promoter/partial protoxin structural gene combination is then placed in a known vector suitable for maintenance in the desired cell type. The promoter/structural gene/vector combination is then transformed by an appropriate technique known in the art into a cell of that cell type or from which that cell type may be derived, and partial protoxin expression may be detected as described above. M. J. Adang and J. D.

Kemp, and R. F. Barker and J. D. Kemp, respectively U.S. Pat. appl. Ser. Nos. 535,354 and 553,786, exemplify expression of the pBt73-10 partial protoxin gene in plant cells under control of T-DNA promoters. The present application exemplifies expression of several partial protoxin gene constructs in *E. coli* cells and minicells under control of a promoter derived from the same Bacillus-expressible complete protoxin gene. Expression of partial protoxin genes under control of natural or synthetic *E. coli* promoters will-be well understood by those of ordinary skill in the art, as will be expression in sporulating cells of the genus Bacillus under control of a protoxin-derived Bacillus promoter,, and expression in other organisms under control of appropriate promoters.

EXAMPLES

The following Examples utilize many techniques well known and accessible to those skilled in the arts of molecular biology; such methods are fully described in one or more of the cited references if not described in detail herein. Enzymes are obtained from commercial sources and are used according to the vendor's recommendations or other variations known to the art. Reagents, buffers and culture conditions are also known to those in the art. Reference works containing such standard techniques include the following: R. Wu, ed. (1979) Meth. Enzymol. 68, R. Wu et al., eds. (1983) Meth. Enzymol. 100 and 101, L. Grossman and K. Moldave, eds. (1980) Meth. Enzymol. 65, J. H. Miller (1972) *Experiments in Molecular Genetics,* R. Davis et al. (1980) *Advanced Bacterial Genetics,* R. F. Schleif and P. C. Wensink (1982) *Practical Methods in Molecular Biology,* and T. Maniatis et al. (1982) *Molecular Cloning,* and R. L. Rodriguez and R. C. Tait (1983), *Recombinant DNA Techniques.* Additionally, R. F. Lathe et al. (1983) Genet. Engin. 4:1–56, make useful comments on DNA manipulations.

Textual use of the name of a restriction endonuclease in isolation, e.g. "BclI", refers to use of that enzyme in an enzymatic digestion, except in a diagram where it can refer to the site of a sequence susceptible to action of that enzyme, e.g. a restriction site. In the text, restriction sites are indicated by the additional use of the word "site", e.g. "BclI site". The additional use of the word "fragment", e.g. "BclI fragment", indicates a linear double-stranded D14A molecule having ends generated by action of the named enzyme (e.g. a restriction fragment). A phrase such as "BclI/SmaI fragment" indicates that the restriction fragment was generated by the action of two different enzymes, here BclI and SmaI, the two ends resulting from the action of different enzymes. Note that the ends will have the characteristics of being "blunt" (fully base-paired) or "sticky" (i.e. having an unpaired single-stranded protuberance capable of base-pairing with a complementary single-stranded oligonucleotide) and that the sequence of a sticky-end will be determined by the specificity of the enzyme which produces it.

Plasmids, and only plasmids, are prefaced with a "p", e.g., pBR322 or pBt73-10, and strains parenthetically indicate a plasmid harbored within, e.g., E. coli HC1Cl (pBt73-10). Deposited strains are listed in Example 6.3.

Example 1

Molecular Cloning 1.1: PBt73-10 and pBt73-3

The crystal protein gene in *Bacillus thuringiensis* var. kurstaki HD-73 is located on a 50 megadalton (MD) plasmid. At least part of the gene is contained in a 6.7 kbp HindIII fragment (J. W. Kronstad et al. (1983) J. Bacteriol. 154:419-428). The 50 MD plasmid was enriched from HD-73 using sucrose gradient centrifugation. A HD-73 library was constructed by first digesting this plasmid DNA with HindIII. The resulting fragments were mixed with and ligated to HindIII-linearized pBR322 (F. Bolivar et al. (1978) Gene 2:95–113) and transformed into *E. coli* HB101. Ampicillin-resistant tetracycline-sensitive transformants were screened by digesting isolated plasmidDNA with HindIII and choosing those clones with 6.7 kilobase pair (kbp) inserts. Colonies containing plasmids pBt73-3 and pBt73-10 were selected from the HD-73 library for further analysis using an insect bioassay. These clones were grown in L-broth and a 250 fold concentrated cell suspension was sonicated and the extract applied to the surface of insect diet. Neonatal *Manduca sexta* (tobacco hornworm) larvae were placed on the diet for one week. Insect larvae fed extracts of strains harboring pBt73-3 or pBt73-10 did not grow and all larvae died in 2 to 5 days. There was no apparent difference between the larvae fed these extracts and those fed insecticidal protein purified from cells of *B. thuringiensis.*

Restriction enzyme analysis (FIG. 1) of pBt73-3 and pBt73-10 showed that the two plasmids had identical 6.7 kbp *B. thuringiensis* DNA fragments inserted into the pBR322 vector in opposite orientations (FIG. 2). Note that pBt73-3 can be converted to pBt73-10 by digestion with HindIII, religation, and transformation into HB101 followed by appropriate selection and screening steps. The two plasmids are functionally equivalent for all manipulations described herein.

pBt73-10 was used to further probe the transformants from the HD-73 plasmid library. Sixteen of the 572 colonies hybridized to the insert of clone pBt73-10 and all had the characteristic 6.7 kbp HindIII fragment. Further restriction enzyme analysis showed these clones to all be one of the two possible orientations in pBR322 of the same DNA fragment. This suggested there could be a single crystal protein gene in strain HD-73. That these clones represent the only insecticidal protein gene in HD-73 was confirmed by hybridizing labeled pBt73-10 probe to Southern blots of HD-73 plasmid DNA digested with HindIII, BglII or SalI. None of these enzymes has a restriction site in our cloned crystal protein gene. Hybridization results showed a single band of *B. thuringiensis* cellular DNA hybridized with pBt73-10 and further indicated that HD-73 has a single insecticidal crystal protein gene. A number of other clones were identified by hybridization with a probe made from pBt73-10. Restriction mapping showed that these clones are all identical to either pBt73-3 or pBt73-10, further supporting the conclusion that the HD-73 has a single crystal protein gene.

1.2: pBt73-161 and pBt73-498

Immunodetection of electrophoretically separated peptides on protein blots and DNA sequencing showed that pBt73-10 and pBt73-3 each contained a partial protoxin gene. To reconstruct a complete protoxin gene, flanking DNA restriction sites were identified by Southern blots of restriction digests, a well-known technique, and overlapping clones were selected from a PstI library made from 50 MD plasmid-enriched DNA as follows. 50 MD plasmid DNA, enriched by sucrose gradient centrifugation as above, was digested to completion with PstI, mixed with and ligated to PstI-linearized pBR322, and transformed into HB101. Tetracycline-resistant transformants were screened essentially as described by W. D. Benton and R. W. Davis (1977) Science 196:180–182, using a probe nick-translated from the 6.7 kbp HindIII insert of pBt73-10. Plasmid DNAs isolated from strains which bound the probe were characterized by restriction enzyme analysis. Two strains choosen for further work harbored pBt73-498 (FIG. 2C), which contains the 5'-end of a crystal protein gene and pBt73-161 (FIGS. 1 and 2A) which contains the 3'-end of a crystal protein gene.

1.3: pBt73-16

The 5'- and 3'-ends of the protoxin gene were fused together at the unique HindIII site to form a complete protoxin gene (FIG. 2). pBt73-10 DNA was digested with BamHI, ligated to itself, and transformed into HB101. Plasmid DNAs from ampicillin-resistant transformants were characterized by restriction enzyme analysis and a strain was identified that harbored a plasmid, designated pBt73-10 (Bam), having single BamHI and HindIII sites due to deletion of a small HindIII site-bearing BamHI fragment. A 5 kbp HindIII fragment of pBt73-161, isolated by agarose gel electrophoresis, was mixed with and ligated to HindIII-digested dephosphorylated (by bacterial alkaline phosphatase) pBt73-10(Bam) DNA. After the ligation mixture was transformed into HB101, plasmid DNA isolated from ampicillin-resistant tetracycline-sensitive transformants was characterized by restriction enzyme analysis. A transformant was identified that harbored a plasmid, designated pBt73-16, carrying a complete protoxin gene (FIG. 1).

1.4: pBt73-3(Ava)

Convenient AvaI restriction sites in clone pBt73-3 were used to remove a 3' segment of the protoxin gene. pBt73-3 DNA was digested with AvaI, ligated to itself, and transformed into HB101. Plasmid DNAs isolated from ampicillin-resistant transformants were characterized by restriction enzyme analysis and a colony harboring a plasmid, designated pBt73-3(Ava), was identified (FIG. 2A).

1.5: pBt73-Sau3AI

50 MD HD-73 plasmid DNA was partially digested with Sau3AI, a restriction enzyme that produces 5'GATC . . . 3' sticky-ends compatible for ligation with sticky-ends produced by the enzymes BamHI, BclI, and BglII. The HD-73 DNA fragments were mixed with and ligated to dephosphorylated BamHI-linearized pBR322, and the ligation mixture was transformed into HB101. Ampicillin-resistant transformants were screened as described in Example 1.2 by the method of Benton and Davis, supra, using the 6.7 kbp HindIII pBt73-10 probe, and a colony was identified that harbored a plasmid designated herein as pBt73-Sau3AI. The insert of pBt73-Sau3AI was about 3 kbp long, carried a partial protoxin gene having removed from its 3'-end Bacillus DNA 3' from the first Sau3Al 3'-from the AvaI site used to construct pBt73-3(Ava).

Example 2

Nucleotide sequence of the crystal protein gene

The complete nucleotide sequence of the protoxin gene from B. thuringiensis var. kurstaki HD-73 is shown in FIG. 3, beginning with an ATG initiation codon at position 388 and ending with a TAG termination condon at position 3.924. The total length of the B. thuringiensis HD-73 gene was 3,537 nucleotides, coding for 1,178 amine acids producing a protein with a molecular weight of 133,344 Daltons (D). The 5'-end of the coding sequence was confirmed experimentally using a coupled DNA-direct in vitro system to form the amino-terminal dipeptide.

The base composition of the protoxin gene, direct repeats, inverted repeats, restriction site locations, and the codon usage are inherent in the disclosed sequence (FIG. 3). There was no bias towards prokaryotic or eukaryotic condon preferences.

Example 3

Expression of completed and partial protoxin genes in *E. coli*

3.1: pSt73-16

Shown in Table 2 are the *E. coli* clones which contain complete or partial protoxin genes. Protein blots of these *E. coli* extracts were used to detect immunologically crystal protein antigen production by these clones (FIG. 3). Plasmid pBt73-16 was shown by DNA sequencing to contain a complete protoxin gene and *E. coli* cells containing this plasmid synthesized a peptide of approximately 130 kD that comigrated during SDS polyacrylamide gel electrophoresis with solubilized protoxin protein and cross-reacted strongly with antiserum to crystal protein. A series of indiscrete peptide bands were observed between this major peptide of 68 kD. High pressure liquid chromatographic analysis indicated that the 68 kD peptide was similar if not identical to the protease-resistant portion of the protoxin. A mini-cell strain was used to analyze the peptide products of pBt73-16. The results were similar to those of the immunoblots indicating a lack of stability of the crystal protein in *E. coli* that results in degradation of the 130 kD peptide to 68 kD.

3.2: pSt37-10 and pBt73-3 pBt73-10 contains the 5'2,825 bp of the HD-73 protoxin gene encoding a partial protoxin peptide sequence of 106, 340 D. Translation should continue into pBR322 encoded sequence for an additional 78 bases, thereby resulting in synthesis of a peptide having a total molecular weight of approximately 106,560 D.

Analyses on the protein produced by the *E. coli* clones showed that pBt73-3 and pBt73-10 encoded soluble antigens that formed a precipitin band with antiserum to *B. thuringiensis* insecticidal protein in Ouchterlony diffusion slides. Cell extracts were analyzed on 10% SDS polyacrylamide gels, transferred to nitrocellulose, and immunological reactions done with antibody and [$^{125}$I]-protein A. No band was found at 130 kD where denatured protoxin is observed, however, a peptide of about 68 kD was seen that binds crystal protein antibody, and was identical in size to activated toxin. A 104 kD peptide was also observed. These peptides accounted for approximately 0.1% of the total *E. coli* protein. High pressure liquid chromatographic analysis indicated that the 68 kD peptide was similar if not identical to the protease-resistant protion of the protoxin. In *E. coli* mini-cells harboring pBt73-10 expressed peptides of approximately 104 kD and 68 kD. These data showed that the 104 kD peptide was not stable in *E. coli* but it was degraded to a relatively stable form of 68 kD.

3.3: pBt73-3(Ava) and pBt73-Sau3AI

*E. coli* containing pBt73-3(Ava)-as constructed encodes an amino-terminal 68,591 D peptide of the protoxin gene along with 32 amino acids encoded by pBR322 for an expected translation product of about 72 kD. *E. coli* extracts containing pBt73-3(Ava) on immunoblots produced a peptide of approximately 68 kD. High pressure liquid chromatographic analysis indicated that the 68 kD peptide was similar if not identical to the protease-resistant portion of the protoxin. *E. coli* mini-cells harboring pBt73-3(Ava) also produced a 68 kD peptide.

Extracts of pBt73-Sau3AI-containing HB11 and mini-cells gave similar results to pBt73-3(Ava) when investigated with immunoblots.

3.4: pBt73-498

A truncated toxin gene is carried by pBt73-498. This plasmid has an N-terminal protoxin peptide of 53,981 D fused to a pBR322 peptide of 2,700 D for an expected peptide totaling approximately 57 kD. In *E. coli* extracts on immunoblots there was a peptide of 45 kD that weakly cross-reacted with antiserum to crystal protein, whereas in the *E. coli* mini-cell, strain pBt73-498 produced a slightly larger peptide of approximately 50 kD. As it is difficult to compare the exact peptide sizes by SDS polyacrylamide gel electrophoresis, the difference in the apparent molecular weights for pBt73-498 peptides may not be significant.

3.5: Common features

That the exact means for translational termination in the pBR322-encoded partial protoxin peptides was not important was demonstrated by the finding that insecticidal activity was encoded by *B. thuringiensis* DNA inserts (pBt73-3 and pBt73-10) having either orientation within the pBR322 vector, and also by pBt73-3(Ava) and pBt73-Sau3A. Presumably the initially translated protoxin amino acid residues carboxy-terminal to the ultimate carboxy-terminus of the toxin were removed in *E. coli* by a proteolytic process similar to that which naturally activates the crystal protein.

Experiments utilizing a coupled DNA-direct in vitro system (H. Weissbach et al. (1984) Biotechniques 2:16–22) determine the amino-terminal dipeptides produced by pBt73-16, pBt73-3, pBt73-10, pBt73-3(Ava), and pBt73-498 indicated that all of these structural genes had the same translational start site, encoding fMet-Asp.

The 68 kD peptides were not distinguished from each other or activated crystal protein toxin by any tests used by the time this application was filed.

Example 4

Properties of the expressed gene products 4.1: Insect bioassays of the *E. coli* clones Table 4 lists the relative toxicities of *E. coli* containing complete or truncated protoxin genes. As expected, pBt73-16 containing the complete gene encodes the product that was the most toxic to *Manduca sexta* larvae. However, pBt73-10, pBt73-Sau3AI (having toxicity about the same as p[]t73-3(Ava)), and pBt73-3(Ava) which expressed the N-terminal 68 kD peptide in *E. coli* were unexpectedly both lethal to the larvae. This indicates the N-terminal 68 kD peptide is sufficient for biological activity. Extracts of *E. coli* cells harboring pBt73-498 were tested at high concentrations. Growth of the larvae was not generally inhibited and extracts were not found to be lethal during the six day course of the bioassay. Bioassay of fractions collected high pressure liquid chromatographic separations of extracts of HD11 strains containing partial protoxin genes showed that the 68 kD peptide was toxic to insect larvae.

4.2: Solution properties of peptides

*E. coli* extracts were fractionated by centrifugation and the resultant fractions were assayed immunologically for crystal protein and its derivatives after SDS-polyacrylamide gel electrophoresis and blotting onto a solid support. Solubility of a particular-sized peptide did not vary with the specific plasmid from which it was derived. The 130 kD protoxin was totally sedimented by a 16,000 x g, 5 min spin, indicating that it was insoluble as would be expected for a crystalline protein. The 68 kD toxin was observed in both the pellet and supernatants of both a 16,000 x g, 5 min spin and a 100,000 x g, 5 min spin. This indicated that it could be highly soluble though it might interact with itself or other *E. coli* extract components, probably because of the extremely hydrophobic nature of its amino acid composition. The 104 kD partial protoxin encoded by pBt73-10 was observed to be totally soluble after both 16,000 x g and 100,000 x g spins, indicating that the solubility properties of the toxic moiety can be manipulated by changing the carboxy-terminal peptide moiety.

Example 5

Discussion and comparison with publications

The protoxin gene from *B. thuringiensis* var. kurstaki HD-73 was cloned and the complete nucleotide sequence of the gene was determined and is disclosed herein. The primary structure consisted of 3,537 nucleotides coding for 1,178 amino acids encoding a protein having a molecular weight of 133,344 Daltons. The crystal protein of *B. thuringiensis* var. kurstaki HD-1-Dipel is reported to contain 1,176 amino acids (approx. mol. wt. 130 kD) (S. Chang (1983) Trends Biotechnol. 1:100–101). The published sequence (H. C. Wong et al. (1983) J. Biol. Chem. 258:1960–1967) available for comparison accounts for less than one-third of the protoxin gene. When the present sequencing data was compared with the partial sequence of the 5'-end of the crystal protein gene from *B. thuringensis* var. kurstaki HD-1-Dipel, 41 differences were found (FIG. 3). All the changes occurred within the gene; only one occurred within the first 600 base paris (bp) at position 831 and the remaining 40 occurred within the last 400 bp of the sequence available for comparison. Twelve of these base changes resulted in amino acid differences. The promoter regions and the 5'-ends of the crystal protein genes were very homologous. The majority of the changes occurred in the last 400 bp of the compared partial sequence. The restriction maps of genes from *B. thuringensis* var. Kurstaki HD-1 (G. A. Held et al., (1982) Proc. Natl. Acad. Sci. USA 77:6065–6069), *B. thuringensis* var. berliner 1715 (A. Klier et al. (1982) EMBO J. 1:791–799), *B. thuringensis* var. kurstaki HD-1-Dipel (H. E. Schnepf and H. R. Whitely (1981) Proc. Natl. Acad. Sci. USA 78:2893–2897), and the map of *B. thuringiasis* var. kurstaki HD-73 described in the present application all differ extensively, indicating portions of the crystal protein gene can vary and yet the protein remains biologically active. The promoter region and 5'-and sequences of the crystal protein genes of HD-1 and HD-73 strains differ completely from the analogous sequences proposed for the chromosomal crystal proteingene of *B. thuringiensis* strain berliner 1715 (A. Klier et al., (1983) Nutl. Acids Res. 11:3973–3987).

Previous S1 nuclease mapping on strain HD-1 has located two possible initiation of transcription start sites and also putative prokaryotic promoter sequences at the −10 positions, but not homology was found to the consensus sequence at the −35 position (Wong et al., supra). They also indicate a prokaryotic ribosome bind site (J. Shine and L. Dalgarno (1974) Proc. Natl. Acad. Sci. USA 71:1342–1346) −3 bases from the ATS initiation condon. Sequences of the promoter regions and the 5'-ands of the crystal protein genes are identical in both HD-1 and HD-73 strains but different than found in berliner (Klier et al. (1983) supra). It is highly probable, due to the highly conserved nature of these regions, that the transcriptional start sites occurs in HD-73 at a similar position of HD-1-Dipel.

In addition to *E. coli* containing a complete crystal protein gene, three plasmids were constructed having various amounts of the 3'-coding sequence deleted. A coupled DNA-directed in vitro system was used as described by H. Weissbach et al. (1984) Biotechniques 2:16–22, to determine the amino-terminal dipeptides of these crystal protein construction. In each plasmid the dipeptide synthesized was fMet-Asp, indicating that the translational start site of each crystal protein construction is 5'. . . . AUGGAPu. . . .3' (Met-Asp). These results agree with the start site observed for *B. thuringiensis* var. kurstaki HD-1-Diepl (Wong et al., supra). A. Klier et al. (1983) supra, reported a completely different translational start site for *B. thuringiensis* var. berliner 1715.

*E. coli* (pBt73-16), which harbors a plasmid bearing a complete crystal protein gene, *E. coli* (pBt73-10), and *E. coli* (pBt73-3(Ava)) all produced a peptide of approximately 68 kD. This corresponds in size to the fragment of the protoxin others have reported to be trypsin-resistant (R. M. Faust et al. (1974) J. Invertebr. Pathol. 24:365-373; T. Yamamoto and R. E. McLaughlin (1981) Biochem. Biophys. Res. Commun. 103:414-421; and H. E. Huber and P. Luthy (1981), in *Pathogenesis of Invertebrate Microbial Diseases,* ed.: E. W. Davidson, pp. 209–234). Experiments using separation of peptides by high pressure liquid chromatography indicated that the 3'-truncated peptides produced by the *E. coli* strains described herein were indistinguishable from the protease-resistant portion of the crystal protein. That extracts of *E. coli* (pBt73-10) or *E. coli* (pBt73-3(Ava)) were less toxic to insects than *E. coli* (pBt73-16) extracts of the complete gene was probably not due to the loss of an active region of the toxin but rather to a lack of stability in *E. coli*. *E. coli* (pBt73-498) produced a 45 kD peptide and was not toxic to insects (Table 2).

Example 6

Experimental 6.61: Materials

Ultra pure urea was obtained from BRL (Gaithersburg, Md.), polyacrylamide from BDH (Poole, England), calf intestinal alkaline phosphatase from Boehringer (Mannheim, W. Germany), polynucleotide kinase from P. L. Biochemicals, Inc. (Milwaukee, Wis.), and [$\gamma$-$^{32}$p] ATP from New England Nuclear (Boston, Massachusetts). The restriction enzymes AccI, AvaI, BamhI, BglI, ClaI, EcoRV, HincII, HpaI, KnI, RsaI, and XmnI were from New England Biolabs (Beverly, Mass.). EcoRi, HindlIl, PstI, XbaI, and XhoI from Promega Biotec (Madison, Wis.) and PvuII from BRL (Gaithersburg, Md.). All enzymes were used in accordance to supplier's specifications. Chemicals used for DNA sequencing reactions were from vendors recommended by A. M. Maxam and W. Gilbert (1980) Meth. Enzymol. 65:499–560. X-omat AR5 X-ray film was supplied as rolls by Eastman Kodak (Rochester, N.Y.). All other reagents were of analytical grade unless otherwise stated.

6.2: Sequencing reactions

All the sequencing reactions were done according to the methods well known in the art, of Maxam and Gilbert, supra, with modifications described by R. F. Barker et al. (1983) Plant Molec. Biol. 2:335–350, and R. F. Barker and J. D. Kemp, U.S. Pat. appl. ser. no. 553,786. Long sequencing gels (20 cm wide, 110 cm in length, and 0.2 mm thick) were used to separate the oligonucleotides. The gel plates were treated with silanes. Using these methods, 500 bp per end-labeled fragment were routinely sequenced.

The strategy used to sequence the crystal protein gene is shown in FIG. 1. pBt73-10 was sequenced initially and found to contain an open reading frame of 2,825 bases from the start of the gene to the HindIII site. pBt73-161 contained a 5.4 kb Psti fragment having the 3' 711 bases of the pBt73-10 gene. The overlapping 1,037 bases of pBt73-10 and pBt73-161 were identical. Those two individual plasmids were then fused at the HindIII site to form pBt73-16. Sequencing across that HindIII site showed that the open reading frame was maintained in pBt73-16. Computer analysis of the sequence data was performed using computer programs made available by Drs. 0. Smithies and F. Blattner (University of Wisconsin, Madison).

6.3: Bacterial strains

*Bacillus thuringiensis* var. kurstaki strain HD-73 (NRRL B-4488) was from the Bacillus Genetics Stock Collection. *B. thuringiensis* var. kurstaki HD-1 (NRRL B-3792) was isolated from Dipel (Abbott Laboratories). *Eschericia coli* strain HB11 (NRRL B-11371) (H. W. Boyer and D. Roulland-Dussoix (1969) J. Mol. Biol. 41:459–472 was used in all transformations except in the mini cell experiments where *E. coli* 984 was used (Example 3.7). *E. coli* HB101 (pBt73-10) is on deposit as NRRL B-15612 (this strain was designated *E. coli* HB101 (pl23158-10) when deposited). *E. coli* HB101 (pBt73-16) is on deposit as NRRL B-15759.

6.4: Preparation of plasmids

Both pBR322 and *B. thuringiensis* plasmid DNA was prepared by an alkaline lysis method (H. C. Birnboim and J. Doly (1979) Nucl. Acids Res. 7:1513–1523). Before cloning, *B. thuringiensis* plasmids were fractionated by centrifugation at 39,000 rpm in a Beckman SW40-1 rotor for 90 min at 15° C. through 5%–25% sucrose gradients containing 0.55 M NaCl, 0.005 M NaEDTA, and 0.05M Tris-HCl, pH8.0 and the fractions analyzed on 0.5% agarose gels. Linearized vector DNAs were usually dephosphorylated by incubation with bacterial alkaline phosphatase before being mixed with and ligated to a DNA intended for insertion into the vector, 6.5: Preparation of antisera to crystal protein

*B. thuringiensis* strains HD-1-Dipel and HD-73 were grown to sporulation in modified G medium (A. I. Aronson et al. (1971) J. Bacteriol. 106:1016–1025 and crystals were purified by three passes in Hypaque-76 (Winthrop) gradients (K. Meenakshi and K. Jayaraman (1979) Arch. Microbiol. 120:9–14), washed with 1M NaCl, deionized water, and lyophilized. Crystals were solubilized in cracking buffer 1% SDS (sodium dodecylsulfate), 2% 2-mercaptoethanol, 6 M urea, 0.01 M sodium phosphate pH 7.2 with 0.02% bromphenol blue by heating at 95° C. for 5 minutes. Electrophoresis was performed by a modification of the procedure of U. K. Laemmli (1970) Nature 227:680–685, as described previously (M. J. Adang and L. K. Miller (1982) J. Virol. 44:782–793). Gels were stained for 5 minutes, and destained 1 hour in deionized water. The 130 kD band was excised, lyophilized, and ground to a powder in a Wigl-Bug Amalgamator (Crescent Manufacturing Company). Rabbits were subcutaneously injected with 50 ng crystal protein, suspended in complete Freund's adjuvant followed by two injections with 50 ng crystal protein each in incomplete adjuvant over a four-week period. Monoclonal antibodies prepared against HD-73 crystal protein gave results identical in interpretation to results obtained with polyclonal sera.

6.6: Immunodetection of blotted peptides

*E. coli* clones were grown overnight in L-broth, pelleted, and brought to a 100 times concentrated suspension with 10 mM NaCl, 10 mM Tris HCl pH 8.0, and 1 mM EDTA containing phenylmethylsulfonyl fluoride (PMSF, a protease inhibitor) to 200 ng/ml. The suspension was sonicated on ice and the extracts stored frozen. Electrophoresis of *E. coli* extracts was as described above and immunodetection of peptides on blot Was according to the procedures of H. Towbin et al. (1979) Proc. Natl. Acad. Sci. USA 76:4350–4354.

6.7: Preparation and labeling of *E. coli* mini-cells

Mini-cells were isolated as described by A. C. Frager and R. Curtiss III (1975) Curr. Top. Microbiol. Imnunol. 69:1–84, labelled with [$^{35}$S]methionine and processed for analysis by SDS-polyacrylamide gel electrophoresis according to the procedures of S. Harayama et al. (1982) J. Bacteriol. 152:372–383.

6.8: Insect bioassays

Insects were obtained from commercial sources and kept essentially as described by R. A. Bell and F. G. Joachim (1976) Ann. Entomol. Soc. Amer. 69:365–373, or R. T. Tamamoto (1969) J. Econ. Entomol. 62:1427–1431. Bioassays for insecticidal protein were done by feeding extracts to larvae of *Manduca sexta* essentially as described by J. H. Schesser et al. (1977) Appl. Environ. Microbiol. 33:878–880. *E. coli* extracts for bioassays did not have PMSF in the sonication buffer.

TABLE I

Insects susceptible to B. thuringiensis insecticidal protein

COLEOPTERA
Popillia japonica (Japanese beetle)
Sitophilus granarius (granary weevil)
DIPTERA
Aedes aegypti (yellow-fever mosquito)
A. atlanticus
A. cantans
A. capsius
A. cinereus
A. communis
A. detritus
A. dorsalis
A. dupreei
A. melanimon
A. nigromaculis (pasture mosquito)
A. punctor
A. sierrensis (western treehole mosquito)
A. sollicitans (brown salt marsh mosquito)
Aedes sp.
A. taeniorhynchus (black salt marsh mosquito)
A. tarsalis
A. tormentor
A. triseriatus
A. vexans (inland floodwater mosquito)
Anopheles crucians
A. freeborni
A. quadrimaculatus (common malaria mosquito)
A. sergentii
A. stephensi
Anopheles sp.
Chironomus plumosus []ironomus: midges, biting)
Chironomus s.
C. tummi
Culex erraticus
C. inornata
C. nigripalus
C. peus C. pipiens (northern house mosquito)
C. quinquefasciatus (C. pipiens fatigans) (southern house mosquito)
C. restuans
Culex sp.
C. tritaeniorhynchus
C. tarsalis (western encephalitis mosquito)
C. territans
C. univittatus
Culiseta incidens (Culiseta: mosquitos)
C. inornata
Diamessa s.
Dixa sp. (Dixa: midges)
Eusimulium (Simulium) latipes (Eusimulium: gnats)
Goeldichironomus holoprasinus
Haematobia irritans (horn fly)
Hippelates collusor
Odagmia ornata
Pales pavida
Polpomyia sp. (Polpomyia: midges, biting)
Polypedilum sp. (Polypedilum: midges)
Psorophora ciliata
P. columiae (confinnis) (Florida Glades mosquito, dark rice field mosquito)
P. ferox
Simulium alcocki (Simulium: black flies)
S. argus
S. cervicornutum
S. damnosum
S. jenningsi
S. piperi
S. tescorum
S. tuberosum
S. unicornutum
S. venustum
S. verecundum
S. vittatum
Uranotaenia inguiculata
U. lowii
Wyeomyia mitchellii (Wyeomyia: mosquitos)
W. vanduzeei
HYMENOPTERA
Athalia rosae (as colibri)
Nematus (Pteronidea) ribesii (imported currantworm)
Neodiprion banksianae (jack-pine sawfly)
Priophorus tristis
Pristiphora erichsonii (larch sawfly)
LEPIDOPTERA
Achaea janata (croton caterpillar)
Achroia grisella (lesser wax moth)
Achyra rantalis (garden webworm)
Acleris variana (black-headed budworm)
Acrobasis sp.
Acrolepia alliella
Acrolepiopsis (Acrolepia) assectella (leek moth)
Adoxophyes orana (apple leaf roller)
Aegeria (Sanninoidea) exitiosa (peach tree borer)
Aglais urticae
Agriopsis (Erannis) aurantiaria (Erannis: loopers)
A. (E.) leucophaearia
A. marginaria
Agrotis ipsilon (as ypsilon) (black cutworm)
A. segetum
Alabama argillacea (cotton leafworm)
Alsophila aescularia
A. pometaria (fall cankerworm)
Amorbia essigana
Anadeyidia (Plusia) peponis.
Anisota senatoria (orange-striped oakworm)
Anomis flava
A. (Cosmophila) sabulifera
Antheraea pernyi
Anticarsia gemmatalis (velvetbean caterpillar)
Apocheima (Biston) hispidaria
A. pilosaria (pedaria)
Aporia crataegi (black-veined whitemoth)
Archips argyrospilus (fruit-tree leaf roller)
A. cerasivoranus (ugly-nest caterpillar)
A. crataegana
A. podana
A. (Cacoecia) rosana
A. xylosteana
Arctia caja
Argyrotaenia mariana (gray-banded leaf roller)
A. velutinana (red-banded leaf roller)
Ascia (Pieris) monuste orseis
Ascotis selenaria
Atteva aurea (alianthus webworm)
Autographa californica (alfalfa looper)
A. (Plusia) gamma
A. nigrisigna
Autoplusia egena (bean leaf skeletonizer)
Azochis gripusalis
Bissetia steniella
Bombyx mori (silkworm)
Brachionycha sphinx
Bucculatrix thurberiella (cotton leaf perforator)
Bupolus piniarius (Bupolus: looper)
Cacoecimorpha pronubana
Cactoblastis cactorum (cactus moth)
Caloptilia (Gracillaria) invariabilis
C. (G) syringella (lilac leaf miner)
C. (G.) theivora
Canephora asiatica
Carposina niponensis
Ceramidia sp.
Cerapteryx graminis
Chilo auricilius
C. sacchariphagus indicus
C. suppressalis (rice stem borer, Asiatic rice borer)
Choristoneura fumiferana (spruce budworm)
C. murinana (fir-shoot roller)
Chrysodeixis (Plusia) chalcites (green garden looper)
Clepsis spectrana
Cnaphalocrocis medinalis
Coleotechnites (Recurvaria) milleri (lodgepole needle miner)
C. nanella
Colias eurytheme (alfalfa caterpillar)
C. lesbia
Colotois pennaria
Crambus bonifatellus (fawn-colored lawn moth, sod webworm)
C. sperryellus
Crambus spp.
Cryptoblabes gnidiella (Christmas berry webworm)
Cydia funebrana
C. (Grapholitha) molesta (oriental fruit moth)
C. (Laspeyresta) pomonella (codling moth)
Datana integerrima (walnut caterpillar)
D. ministra (yellow-necked caterpillar)
Dendrolimus pini
D. sibiricus
Depressaria marcella (a webworm)

Desmia funeralis (grape leaf folder)
Diachrysia (Plusia) orichalcea (a semilooper)
Diacrisia virginica (yellow woollybear)
Diaphania (Margaronia) indica
D. nitidalis (pickleworm)
Diaphora mendica
Diatraea grandiosella (southwestern corn borer)
D. saccharalis (sugarcane borer)
Dichomeris marginella (juniper webworm)
Drymonia ruficornis (s chaonia)
Drymonia sp.
Dryocampa rubicunda (greenstriped mapleworm)
Earias insulana
Ectropis (Boarmia) crepuscularia
Ennomos subsignarius (elm spanworm)
Ephestia (Cadra) cautella (almond moth)
E. elutella (tobacco moth)
E. (Anagasta) kuehniella (Mediterranean flour moth)
Epinotia tsugana (a skeletonizer)
Epiphyas postvittana
Erannis defoliaria (mottled umber moth)
E. tiliaria (linden looper)
Erinnysis ello
Eriogaster henkei
E. lanestris
Estigmene acrea (salt marsh caterpillar)
Eublemma amabilis
Euphydryas chalcedona
Eupoecilia ambiguella
Euproctis chrysorrhoea (Nygmi phaeorrhoea) (brown tail moth)
E. fraterna
E. pseudoconspersa
Eupterote fabia
Eutromula (Simaethis) pariana
Euxoa messoria (dark-sided cutworm)
Galleria mellonella (greater wax moth)
Gastropacha quercifolia
Halisdota argentata
H. caryae (hickory tussock moth)
Harrisina brillians (western grapeleaf skeletonizer)
Hedya nubiferana (fruit tree tortrix moth, green budworm)
Heliothis (Helicoverpa) armigera (Heliothis=Chloridea) (gram pod borer)
H. (H.) assulta
Heliothis peltigera
H. virescens (tobacco budworm)
H. viriplaca
H. zea (cotton bollworm, corn earworm, soybean podworm, tomato fruitworm, sorghum headworm, etc.)
Hellula undalis (cabbage webworm)
Herpetogramma phaeopteralis (tropical sod webworm)
Heterocampa guttivitta (saddled prominent)
H. manteo (variable oak leaf caterpillar)
Holcocera pulverea
Homoeosoma electellum (sunflower moth)
Homona magnanima
Hyloicus pinastri
Hypeuryntis coricopa
Hyphantria cunea (fall webworm)
Hypogymna morio
Itame (Thamnonoma) wauaria (a spanworm)
Junonia coenia (buckeye caterpillars)
Kakivoria flavofasciata
Keiferia (Gnorimoschema) lycopersicella (tomato pinworm)
Lacanobia (Polia) oleracea
Lamdina athasaria pellucidaria
L. fiscellaria fiscellaria (hemlock looper)
L. fisellaria lugubrosa (western hemlock looper)
L. fiscellaria somniaria (western oak looper)
Lampides boeticus (bean butterfly)
Leucoma (Stilpnotia) salicis (satin moth)
L. wiltshirei
Lobesia (=Polychrosis) botrana
Loxostege commixtalis (alfalfa webworm)
L. sticticalis (beet weuworm)
Lymantria (Porthetria) dispar (gypsy moth) (Lymantria: tussock moths)
L. monacha (nun-moth caterpillar)
Malacosoma americana (eastern tent caterpillar)
M. disstria (forest tent caterpillar)
M. fragilis (=fragile) (Great Basin tent caterpillar)
M. neustria (tent caterpillar, lackey moth)
M. neustria var. testacea
M. pluviale (western tent caterpillar)
Mamerstra brassicae (cabbage moth)
Manduca (Inotoparce) quinquemaculata (tomato hornworm)
M. (I.) sexta (tobacco hornworm)
Maruca testulalis (bean pod borer)
Melanolophia imitata
Mesographe forficalis
Mocis repanda (Mocis: semilooper)
Molippa sabina
Monema flavescens
Mythimna (Pseudaletia) unipuncta (armyworm)
Nephantis serinopa
Noctua (Triphaena) pronuba
Nomophila noctuella (lucerne moth)
Nymphalis antiopa (mourning-cloak butterfly)
Oiketicus moyanoi
Ommatopteryx texana
Operophtera brumata (winter moth)
Opsophanes sp.
O. fagata
Orgyia (Hemerocampa) antiqua (rusty tussock moth)
O. leucostigma (white-marked tussock moth)
O. (H.) pseudotsugata (Douglas-fir tussock moth)
O. thyellina
Orthosia gothica
Ostrinia (Pyrausta) nubilalis (European corn borer)
Paleacrita vernata (spring cankerworm)
Paulmnene juliana
Pandemis dumetana
P. pyrusana
Panolis flamnea
Papilio cresphontes (orange dog)
P. demoleus
P. philenor
Paralipsa (Aphemia) gularis
Paralobesia viteana
Paramyelois transitella
Parnara guttata
Pectinophora gossypiella (pink bollworm)
Pericallia ricini
Peridroma saucia (variegated cutworm)
Phalera bucephala
Phlogophora meticulosa
Phryganidia californica (California oakworm)
Phthorimaea (=Gnorimoschema) operculella (potato tuberworm)
Phyllonorycter (Lithocolletis) blancardella (spotted tentiform leafminer)
Pieris brassicae (large white butterfly)
P. canidia sordida P. rapae (imported cabbageworm, small white butterfly)
Plathypena scabra (green cloverworm)
Platynota sp.
P. stultana
Platyptilia carduidactyla (artichoke plume moth)
Plodia interpunctella (Indian-meal moth)
Plutella xylostella as maculipennis (diamondback moth)
Prays citri (citrus flower moth)
P. oleae (olive moth)
Pseudoplusia includens (soybean looper)
Pygaera anastomosis
Rachiplusia ou
Rhyacionia buoliana (European pine shoot moth)
Sabulodes caberata (omnivorous looper)
Samia cynthia (cynthia moth)
Saturnia pavonia
Schizura concinna (red-humped caterpillar)
Schoenobius bipunctifer
Selenephera lunigera
Sesamia inferens
Sibine apicalis
Sitotroga cerealella (Angoumois grain moth)
Sparganothis pilleriana
Spilonota (Tmetocera) ocellana (eye-spotted budmoth)
Spilosoma lubricipeda (as menthastri)
S. virginica (yellow woollybear)
Spilosoma sp.
Spodoptera (Prodenia) eridania (southern armyworm)
S. exigua (beet armyworm, lucerne caterpillar)
S. frugiperda (fall armyworm)
S. littoralis (cotton leafworm)
S. litura
S. mauritia (lawn armyworm)
S. (P.) ornithogalli (yellow-striped armyworm)
S. (P.) praefica (western yellowstriped armyworm)
Syllepte derogata
S. silicalis
Symmerista canicosta
Thaumetopoea pityocampa (pine processionary caterpillar)
T. processionea
T. wauaria (currant webworm)
T. wilkinsoni
Thymelicus lineola (European skipper)
Thyridopteryx ephemeraeformis (bagworm)
Tineola bisselliella (webbing clothes moth)
Tortrix viridana (oak tortricid)
Trichoplusia ni (cabbage looper)
Udea profundalis (false celery leaftier)
U. rubigalis (celery leaftier, greenhouse leaftier)
Vanessa cardui (painted-lady)
V. io
Xanthopastis timais
Xestia (Amathes, Agrotis) c-nigrum (spotted cutworm)
Yponomeuta cognatella (=Y. evonymi) (Yponomeuta= Hyponomeuta)
Y. evonymella
Y. mahalebella
Y. malinella (small ermine moth)
Y. padella (small ermine moth)
Y. rorrella
Zeiraphera diniana
MALLOPHAGA
Bovicola bovis (cattle biting louse)
B. crassipes (Angora goat biting louse)
B. limbata
B. ovis (sheep biting louse)
Lipeurus caponis (wing louse)
Menacnathus stramineus (chicken body louse)
Menopon gallinae (shaft louse)
TRICHOPTERA
Hydropsyche pellucida
Potamophylax rotundipennis

TABLE 2

Plants recommended for protection by *B. thuringinensis* insecticidal protein

| | | |
|---|---|---|
| alfalfa | escarole | potatoes |
| almonds | field corn | radishes |
| apples | filberts | rangeland |
| artichokes | flowers | raspberries |
| avocados | forage crops | safflower |
| bananas | forest trees | shade trees |
| beans | fruit trees | shingiku |
| beets | garlic | small grains |
| blackberries | grapes | soybeans |
| blueberries | hay | spinach |
| broccoli | kale | squash |
| brussels sprouts | kiwi | stonefruits |
| cabbage | kohlrabi | stored corn |
| caneberries | lentils | stored grains |
| carrots | lettuce | stored oilseeds |
| cauliflower | melons | stored peanuts |
| celery | mint | stored soybeans |
| chard | mustard greens | stored tobacco |
| cherries | nectarines | strawberries |
| chinese cabbage | onions | sugarbeets |
| chrysanthemums | oranges | sugar maple |
| citrus | ornamental trees | sunflower |
| collards | parsley | sweet corn |
| cos lettuce | pasture | sweet potatoes |
| cotton | peaches | tobacco |
| cranberries | peanuts | tomatoes |
| crop seed | pears | turf |
| cucumbers | peas | turnip greens |
| currants | pecans | walnuts |
| dewberries | peppers | watermelons |
| eggplant | pome fruit | |
| endive | pomegranite | |

TABLE 3

Varieties of *B. thuringiensis*
alesti
aizawai
canadensis
dakota
dartnstadiensis
dendrolimus
entomocidus
finitimus
fowleri
galleriae
indiana
israelensis
kenyae
kurstaki
kyushuensis
morrisoni
ostriniae
pakistani
sotto
thompsoni
thuringiensis
tolworthi
toumanoffi
wuhanensis

TABLE 4

| Plasmid | No. of nucleotides in coding sequence | Predicted mol. wt. of product (D) | Determined mol. wt. (kD), E. coli extracts | Determined mol. wt. (kD), mini-cells | Relative[A] Toxicity |
|---|---|---|---|---|---|
| pBt73-16 | 3537 | 133,344 | 130/68 | 130/68 | 100 |
| pBt73-10 | 2825 | 106,340 | 68 | 104/68 | 6 |
| pBt73-3(Ava) | 1836 | 68,591 | 68 | 68 | 6 |
| pBt73-498 | 1428 | 53,981 | 45 | 50 | 0 |

[A]Based on a comparison of $LD_{50}$ values for *E. coli* extracts assayed against *M. sexta* larvae. Extracts of *E. coli* HB101 (pBt73-16) equal 100 by definition.

What is claimed is:

1. A cell containing a recombinant DNA molecule comprising a DNA segment encoding a partial *Bacillus thuringiensis* δ-endotoxin protoxin, the partial protoxin encoding sequence being sufficient to encode a complete toxin, said partial protoxin encoding sequence being terminated by DNA naturally functional in a eukaryotic cell comprising a stop codon in frame and a polyadenylation site 3' to the stop codon.

* * * * *

UNITED STATES PATENT AND TRADEMARK OFFICE
CERTIFICATE OF CORRECTION

PATENT NO. : 6,251,656 B1
DATED : June 26, 2001
INVENTOR(S) : Michael J. Adang

It is certified that error appears in the above-identified patent and that said Letters Patent is hereby corrected as shown below:

Column 1,
Line 45, "protexin" should read -- protoxin --.

Column 2,
Line 22, "crystalline end in" should read -- crystalline endotox --.

Column 3,
Line 40, "protein" should read -- protoxin --.

Column 5,
Line 28 "540..." should read -- 5´... --;
Line 39, "transcript Underlying" should read -- transcript. Underlying --.

Column 6,
Line 56, "31-deletion" should read -- 3´-deletion --.

Column 7,
Lines 18-19, "protoxin generating naturally-occurring" should read -- protoxin gene having naturally-occurring --.

Column 8,
Line 7, "is-isolating" should read -- isolated --;
Line 12, "protoxin-gene" should read -- protoxin gene --;
Line 36, "promoter,," should read -- promoter, --;
Line 67, "D14A" should read -- DNA --.

Column 9,
Line 15, "HClCl" should read -- HB101 --.

Column 11,
Line 12, "amine acids" should read -- amino acids --;
Line 19, "condon" should read -- codon --;
Line 26, "pSt73-16" should read -- pBt73-16 --;
Line 45, "pSt37-10" should read -- pBt73-10 --;
Line 46, "5´2,825" should read -- 5´ 2,825 --.

UNITED STATES PATENT AND TRADEMARK OFFICE
CERTIFICATE OF CORRECTION

PATENT NO.   : 6,251,656 B1
DATED        : June 26, 2001
INVENTOR(S)  : Michael J. Adang It is certified that error appears in the above-identified patent and that said Letters Patent is hereby corrected as shown below:

Column 12,
Lines 14 and 65, "HB11" should read -- HB101 --;
Line 57, "p[ ]t73-3" should read -- pBt73-3 --.

Column 13,
Line 46, "thuringensis" should read -- thuringiensis --;
Line 52, "thuringiasis" should read -- thuringiensis --;
Line 55, "5´-and" should read -- 5´-end --;
Line 58, "proteingene" should read -- protein gene --;
Line 63, "not homology" should read -- no homology --;
Line 67, "ATS" should read -- ATG --.

Column 14,
Line 1, "5´-ands" should read -- 5´-ends --;
Line 16, "Diepl" should read -- Dipel --;
Line 44, "6.61: Materials" should read -- 6.1:  Materials --;
Line 50, "Bamhi" should read -- BamHI --;
Line 50, "AvaI" should read -- AvaI --;
Line 51, "KnI" should read -- KpnI --;
Line 52, "EcoRi" should read -- EcoRI --.

Column 15,
Line 7, "HindlIl" should read -- HindIII --;
Line 8, "Psti" should read -- PstI --;
Line 21, "HB11" should read -- HD-1 --;
Line 26, "(p123158-10)" should read -- (p123/58-10) --.

Column 16,
Line 6, "Was according" should read -- was according --;
Line 61, "[ ]ironomus: midges," should read -- (Chironomus: midges, --;
Line 62, "Chironomus s." should read -- Chironomus sp. --.

Column 17,
Line 12, "Diamessa s." should read -- Diamessa sp. --.

UNITED STATES PATENT AND TRADEMARK OFFICE
CERTIFICATE OF CORRECTION

PATENT NO.    : 6,251,656 B1
DATED         : June 26, 2001
INVENTOR(S)   : Michael J. Adang It is certified that error appears in the above-identified patent and that said Letters Patent is hereby corrected as shown below:

Column 19,
Line 10, "(s chaonia)" should read -- (as chaonia) --.

Column 20,
Line 9, "weuworm" should read -- webworm --;
Line 45, "Paulmnene" should read -- pammene --.

Column 22,
Line 47, "dartnstadiensis" should read -- darmstadiensis --.

Signed and Sealed this

Eighth Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,251,656 B1
DATED : June 26, 2001
INVENTOR(S) : Michael J. Adang

It is certified that error appears in the above-identified patent and that said Letters Patent is hereby corrected as shown below:

Column 23,
Line 17, "8-endotoxin" should read -- δ-endotoxin --.

Signed and Sealed this

Twenty-seventh Day of May, 2003

JAMES E. ROGAN
*Director of the United States Patent and Trademark Office*